United States Patent
Kugelmann et al.

(10) Patent No.: US 9,095,499 B2
(45) Date of Patent: Aug. 4, 2015

(54) BAG HAVING FLOW EQUALIZATION

(71) Applicant: Fresenius Medical Care Deutschland GmbH, Bad Homburg (DE)

(72) Inventors: Franz Kugelmann, St. Wendel/Bliesen (DE); Claus Haupert, Nalbach (DE); Joern Hoermann, Heusweiler (DE)

(73) Assignee: FRESENIUS MEDICAL CARE DEUTSCHLAND GmbH, Bad Homburg (DE)

( * ) Notice: Subject to any disclaimer, the term of this patent is extended or adjusted under 35 U.S.C. 154(b) by 155 days.

(21) Appl. No.: 13/866,268

(22) Filed: Apr. 19, 2013

(65) Prior Publication Data
US 2013/0281963 A1   Oct. 24, 2013

Related U.S. Application Data

(60) Provisional application No. 61/635,583, filed on Apr. 19, 2012.

(30) Foreign Application Priority Data

Apr. 19, 2012   (DE) .......................... 10 2012 007 697

(51) Int. Cl.
*A61J 1/10* (2006.01)
*A61J 1/14* (2006.01)
(Continued)

(52) U.S. Cl.
CPC ...... *A61J 1/10* (2013.01); *A61J 1/1443* (2013.01); *A61J 1/2093* (2013.01); *A61M 1/167* (2014.02); *A61M 1/1656* (2013.01); *A61M 1/1666* (2014.02); *A61M 1/287* (2013.01); *B65D 77/04* (2013.01); *B65D 77/06* (2013.01); *B65D 81/3272* (2013.01); *A61J 2001/202* (2013.01);
(Continued)

(58) Field of Classification Search
CPC .............. A61J 1/2093; A61J 2001/202; A61J 2001/2024; A61J 2001/2027; A61J 1/1443; A61J 2001/145; A61J 2001/1456; A61J 1/20; A61J 1/10; A61M 1/28; A61M 1/282; A61M 1/284; A61M 1/287; A61M 1/1654; A61M 1/1656; A61M 1/1666; A61M 1/1668; A61M 1/167; A61M 5/1483; A61M 5/1486; B65D 81/3272; B65D 35/22; B65D 75/323; B65D 75/324; B65D 75/327; B65D 75/328; B65D 75/367; B65D 75/368; B65D 77/08; B65D 81/3261; B65D 81/3283; B65D 88/1643; B65D 88/1662; B65D 2577/041; B65D 2577/042; B65D 2577/043; B65D 2577/045; B65D 77/04; B65D 77/06; B65D 77/062; B65D 81/3266
See application file for complete search history.

(56) References Cited

U.S. PATENT DOCUMENTS 3,950,158 A * 4/1976 Gossett ............................ 62/4
4,229,299 A   10/1980 Savitz
(Continued)

FOREIGN PATENT DOCUMENTS

DE   19510759     10/1996
DE   697 05 816   4/2002
(Continued)

*Primary Examiner* — Adam Marcetich
(74) *Attorney, Agent, or Firm* — Jacobson Holman, PLLC.

(57) ABSTRACT

The subject matter of the invention is a container system having an inner container for receiving ready-to-use liquid, in particular dialysis liquid, and an outer container surrounding the inner container to receive spent liquid such that the inner container has through-openings which establish a fluidic connection for the liquid in the outer container.

17 Claims, 4 Drawing Sheets

Figure 1:
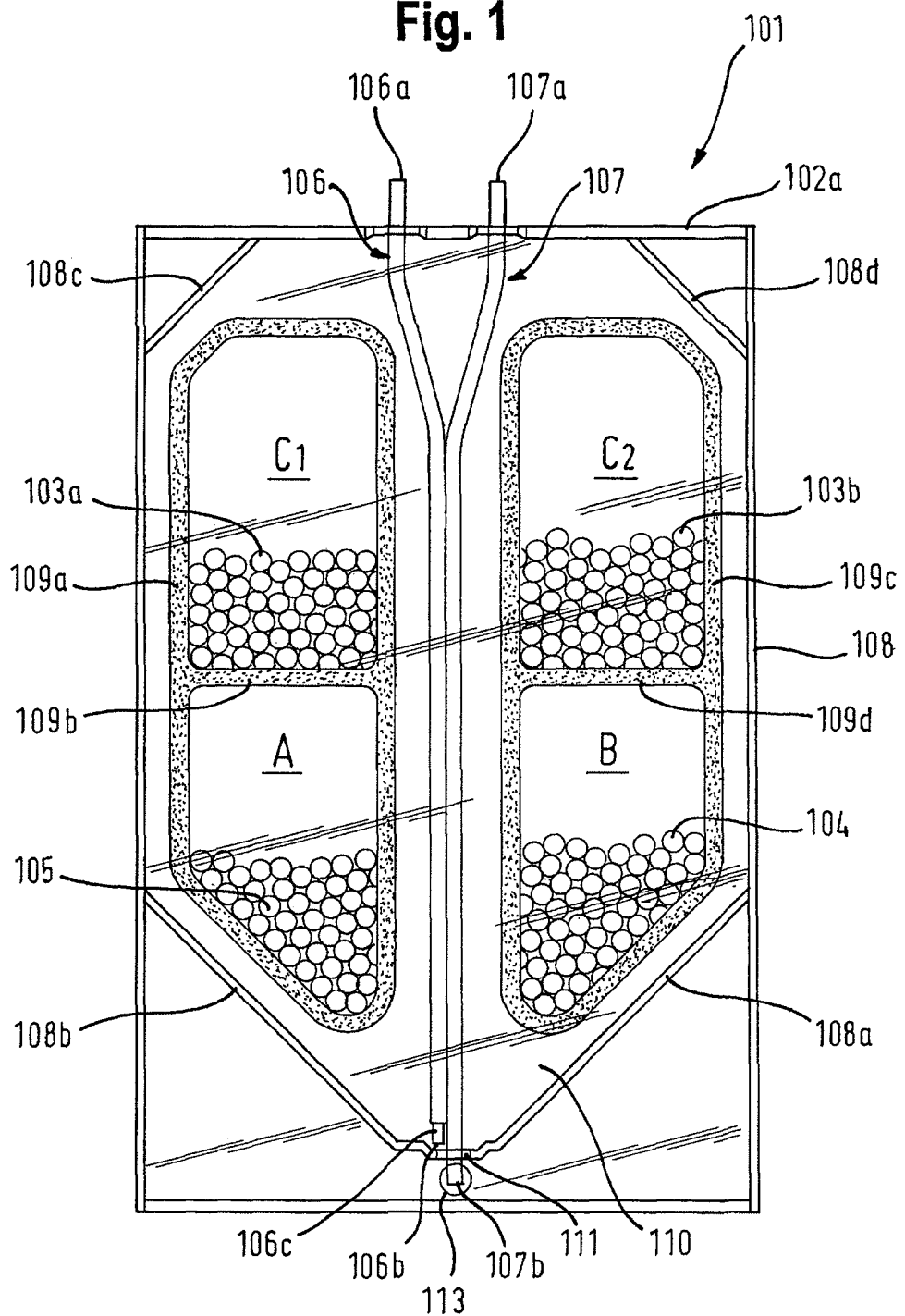

(51) Int. Cl.
*B65D 81/32* (2006.01)
*A61M 1/28* (2006.01)
*B65D 77/04* (2006.01)
*B65D 77/06* (2006.01)
*A61M 1/16* (2006.01)
*A61J 1/20* (2006.01)

(52) U.S. Cl.
CPC ... *A61J 2001/2024* (2013.01); *A61J 2001/2027* (2013.01); *B65D 2577/041* (2013.01); *B65D 2577/042* (2013.01); *B65D 2577/043* (2013.01)

(56) References Cited

U.S. PATENT DOCUMENTS

| | | | |
|---|---|---|---|
| 4,396,382 A * | 8/1983 | Goldhaber | 604/28 |
| 4,522,640 A * | 6/1985 | Jagoe, III | 62/4 |
| 4,767,526 A | 8/1988 | Vantard | |
| 5,263,929 A * | 11/1993 | Falcone et al. | 604/89 |
| 5,810,202 A * | 9/1998 | Hoback et al. | 222/95 |
| 5,843,049 A * | 12/1998 | Heilmann et al. | 604/275 |
| 6,096,007 A * | 8/2000 | Haan et al. | 604/147 |
| 6,135,989 A * | 10/2000 | Atad et al. | 604/410 |
| 6,241,717 B1 * | 6/2001 | Niedospial, Jr. | 604/408 |
| 6,484,514 B1 * | 11/2002 | Joseph et al. | 62/4 |
| 2002/0091371 A1 | 7/2002 | Ritter | |
| 2009/0025706 A1 * | 1/2009 | Cho et al. | 126/263.07 |
| 2009/0320684 A1 * | 12/2009 | Weaver et al. | 96/12 |
| 2012/0199205 A1 * | 8/2012 | Eyrard et al. | 137/1 |
| 2012/0288572 A1 * | 11/2012 | Kugelmann et al. | 424/678 |
| 2012/0310150 A1 * | 12/2012 | Brandl et al. | 604/29 |

FOREIGN PATENT DOCUMENTS

| | | |
|---|---|---|
| DE | 101 00 549 | 7/2002 |
| EP | 0004600 | 10/1979 |
| WO | WO 97/37628 | 10/1997 |
| WO | WO 2011/073274 | 6/2011 |

* cited by examiner

BAG HAVING FLOW EQUALIZATION

BACKGROUND OF THE INVENTION

1. Field of the Invention

The invention relates to the field of preparation and storage of ready-to-use liquid for renal therapy. The invention relates in particular to a bag system for preparing and holding fresh and spent dialysis liquid. In addition, one subject of the invention is a multi-chamber bag for holding concentrates and for preparing a medical solution of the concentrates, as well as a method for preparing a medical solution from several concentrates.

2. Description of the Related Art

Renally insufficient patients suffer from restricted kidney function which prevents the required elimination of substances that are eliminated in the urine from the patient's body. For these patients, toxic metabolites must be removed by purifying their blood in a dialysis treatment.

In dialysis, the blood is purified via a mass exchange membrane which comes in contact with the patient's blood on one side and with a cleaning liquid on the other side. The cleaning liquid is a so-called dialysis solution which receives the substances intended for separation and conveys them out of the patient's blood. Dialysis solutions in general consist of an aqueous composition of physiologically important dissolved components, for example, electrolytes, buffers and osmotically active reagents such as glucose.

In peritoneal dialysis (PD), the dialysis solution is infused into the peritoneum of the patient. The patient's peritoneum serves as a mass exchange membrane through which the blood is purified. In the course of treatment or toward the end of treatment the peritoneum is emptied and the dialysis solution is discarded.

In hemodialysis (HD) the patient's blood to be purified is passed through an extracorporeal blood circulation and brought in contact with an artificial mass exchange membrane. The opposite of the mass exchange membrane is brought in contact with dialysis solution, so that substances which pass through the membrane can be removed from the blood by crossing the membrane with the dialysis solution.

In cases of both HD and PD dialysis the dialysis solutions contain typical dissolved substances such as:
- Electrolytes Na, K, Mg, Ca to maintain an acceptable electrolyte balance in the patient
- Buffers (for example, bicarbonate, acetate, lactate, etc.)
- Glucose (or other osmotic agents) as osmotic agents in peritoneal dialysis or to maintain the blood sugar level during hemodialysis
- Acids or salts of acids (for example, HCl and/or chloride, acetic acid and/or acetate, citric acid and/or citrate) which may contribute toward neutralization of basic partial dialysis solutions or are present as counterions in the electrochemical equilibrium.

In hemodialysis, partial solutions or partial concentrates are often mixed in the dialysis machine before and during the course of the treatment in preparing a finished dialysis solution. Partial concentrates in solid or liquid form are frequently used for this. These are held in individual containers and are diluted by connection to the dialysis machine with the help of a prepared hydraulic system, then are mixed and prepared to yield the ready-to-use dialysis solution.

In another variant, dialysis solutions are prepared in a batch in a step preceding the treatment. The batch is stored in a tank that has been prepared for being connected to a dialysis machine. In many cases, the tank is an integral component of a dialysis treatment unit. In other embodiments, the dialysis tank is separate from the treatment station and is designed to be functionally mobile. The use of a tank with dialysis liquid may thus offer the advantage of being able to select the treatment site to be relatively independent of the location by one-time preparation of the dialysis liquid. Treatment stations at different locations can thus be used without having to rely on a preparation unit for dialysis solution or a water connection to supply the water needed to dilute the concentrates. In these cases, the dialysis solution is mixed from concentrates on an equipment unit provided for this purpose and then is stored, usually in a mobile tank.

In addition, there are known container systems whose ready-to-use solution is placed in a container and this container, e.g., as an inner bag is enclosed by another container. Such concepts are known from beverage technology in particular and are described as "bag in a box" systems, among others.

Systems that have been developed further in the field of dialysis therapy are systems in which the inner container holds the ready-to-use liquid and the container surrounding the inner vessel is prepared for receiving the spent liquid. The inner vessel is then surrounded by the spent liquid in the outer container.

U.S. Pat. No. 4,386,634 describes a container system for preparing a ready-to-use solution for hemodialysis. The ready-to-use solution is prepared in a film bag having a large inner volume by dissolving concentrates. The inner bag is surrounded by water in the outer container.

DE 195 10 759 describes a container system consisting of an inner film bag of a large volume and a flexurally rigid container surrounding the inner bag. The ready-to-use dialysis liquid is placed in the inner bag first and the spent liquid is filled into the space between the inner bag and the outer surrounding container.

WO 2011/073274 describes a bag system with an inner bag and an outer bag surrounding the inner bag. The dialysis liquid is prepared by dissolving the concentrates in the inner bag. Spent dialysis liquid is filled into the space between the inner bag and the outer bag. The entire bag system may additionally be inserted into a flexurally rigid supporting apparatus.

The inner flexible container in the container systems described in the state of the art can have a negative influence on the flow conditions in the outer container due to the development of folds or due to the fact that its position in the space of the surrounding container is not fixed. In particular the inner bag may cover the incoming flow area of the outer container, so that incoming spent liquid is prevented from entering the outer container. In addition, the mobile inner bag may prevent the incoming spent liquid from being uniformly distributed in the outer container. It is possible that initially only portions of the outer container are filled with the oncoming flow of spent liquid. Due to the growing hydrostatic pressure, the inner bag may be displaced suddenly, resulting in an equally sudden equalization of flow in the outer container, which may lead to unacceptable vibrations of the entire apparatus and unacceptably high stress on the material.

A first measure which can prevent excessive mobility of the inner bag in the outer container has already been described in WO 2011/073274 in which it is disclosed that the edges of the inner bag may be welded to the edges of the surrounding bag along a welding line. The inner bag is secured in the outer bag around the circumference in this way. However, it has been found that this measure is also inadequate for achieving uniform filling of the outer container.

The object was therefore to refine a container system for the production and/or storage of ready-to-use liquids or spent liquids with an inner bag and a container surrounding the inner bag so that when liquid is supplied to the outer container, a good equalization of flow is created, so that the container is uniformly filled with an increase in the filling.

DESCRIPTION OF THE INVENTION

The invention is based on the object of refining a container system consisting of an inner container and an outer container surrounding the inner container for holding, preparing or producing medical liquids, in particular liquids for extracorporeal treatment of blood or for renal therapy so that a uniform filling of the outer container is ensured.

This object is achieved by the subject of claim 1, a container system for preparing, processing and holding ready-to-use and/or spent medical liquids, in particular ready-to-use and spent liquids such as those which occur in extracorporeal blood treatment or renal therapy. Advantageous embodiments are represented by features of the subclaims.

The container system according to the invention is formed by an inner container and an outer container surrounding the inner container. The inner container and the outer container each form a closed volume so that they are prepared to receive liquids. Each of the respective containers has access ports through which the container can be filled with liquid or through which liquid can be removed from the respective container. The liquid may be a diluting liquid, i.e., water or aqueous solutions of electrolytes and/or osmotics and/or active ingredients. The solutions may also be ready-to-use solutions prepared for renal therapy. This includes in particular liquids used for peritoneal dialysis, hemodialysis, hemofiltration, hemodiafiltration and other extracorporeal supporting renal therapy methods.

The inner container surrounded by the outer container also has one or more through-openings which bring parts of the volume of the outer bag together in a fluidic connection. The term container is not just limited to the interior area of a vessel accessible to a liquid. Parts of the container which do not belong to the interior space, e.g., due to being welded off and which are not accessible to a liquid are also included in this definition of the term container. The through-openings may also be arranged in areas of the inner container which are not accessible for liquid in the inner container but which would also constitute a flow barrier for liquids in the surrounding container. Such through-openings may be understood to include tubular components, e.g., of a flexurally rigid injection molding material, a flexible length of tubing or a collapsible length of film tubing. However, simple, i.e., circular openings in opposing regions of the container material of the inner container are preferred. By welding along the circular contour, the interior volume of the inner bag is delineated and closed with respect to the outer bag. However, liquid can still flow through the through-openings in the inner bag from one part of the outer bag into another part of the outer container, for example, on the opposite side. The inner container thus presents a lower barrier with respect to any flow equalization required in the outer container. The processes of filling and removing liquid are therefore improved.

One or more through-openings for the container system may be provided. This also depends on the total volume of the inner and/or outer container to be achieved. In particular with small volumes of 5 liters of the container system, for example, only one through-opening may be provided. With large volumes of 120 liters, for example, flow equalization through only one through-opening is uncertain and therefore a plurality of such through-openings must be provided. In certain embodiments the subjects according to the invention may be applied to container systems having volumes of 60 liters±20 liters.

In preferred embodiments, the containers are embodied as bags. A container system may consist of an outer flexurally rigid container and an inner container made of flexible film material in at least some sections, forming a bag. Alternatively the inner container may also be made of a flexurally rigid material and the outer container may be made of a flexible film material in at least some sections and form a bag. In another preferred embodiment, the inner container and the outer container are made of flexible film material in at least some sections and each forms a bag.

The term "bag" in this context is understood to refer to vessels consisting of flexible bordering surfaces, so that they are collapsed when not filled and are unfolded when filled. Such containers having bordering surfaces made of a flexurally rigid material in at least some sections but having on the whole a collapsible character due to flexible bordering surfaces are also included in the sense of this definition.

In one embodiment the inner bag is in a volume defined by the outer bag. It is advantageous if the inner bag is connected to the outer bag at fastening points or lines. This makes it possible to prevent the inner bag from being folded in an unwanted manner, for example, in the empty state, and these folds then make it difficult or impossible to fill the inner bag with liquid. In the worst case, the inner bag cannot unfold and only a minimum of the filling volume that is to be achieved is reached. The fastening of the inner bag to the outer bag may be accomplished, for example, by film pieces which join the outer bag and the inner bag through welding. Alternatively, it is possible to provide that the inner bag and the outer bag are joined to one another by weld lines. These may be, for example, the circumferential welds on the bag. Alternatively, a first film sheeting of the outer bag may be welded either permanently or detachably (peelably) to a first film sheeting of the inner bag.

Peelable welded connections in this context are understood to be the connecting points of two joining partners which exert an adhesive effect on one another after a heat treatment and contact pressure. In the present case, the joining partners are two opposing film pieces of a bag which are joined together by the influence of heat and contact pressure in the welding process using a welding bar. The welding temperature determines the force with which the peel seam can be opened. A peel seam is understood to be an adhesive bond, which can be released again by applying a force without completely tearing the film material. In special embodiments, a peel connection may also be understood to be a connection which causes a partial delamination of a multilayer film laminate by the application of force. In these cases, it is important that the delamination tear does not cause complete failure of the film material that would render the bag useless.

Vent ports are provided on the respective inner and outer bags to further facilitate the process of filling or removing liquid. These ports have a hydrophobic membrane whose pore size is so small that microorganisms or toxins are prevented from crossing the membrane. The hydrophobic membrane material permits an adequate blocking effect in random contact with dialysis liquids, so that no dialysis liquid can penetrate to the outside. In filling the inner bag with a diluting liquid in particular, the air contained therein can escape through the port due to the influx of diluting liquid through the port. Air is also forced out of the outer bag by the expansion of the inner bag in particular. Alternatively, residual air will also escape from the outer bag through the venting membrane in filling the outer bag with dialysis solution that has already been used. Vent ports are indispensable if the container system is flexurally rigid materials. In the extreme case, such container systems are not collapsible, and a corresponding quantity of air or an alternative gas must be resupplied accordingly to equalize the pressure in filling and withdrawing liquids.

The container system made of flexible film material may be made of four films arranged one above the other. The films are secured by a peripheral bordering line. The bordering line may be formed from a weld in some sections or completely, e.g., one or more welds. The welded connection may be accomplished on an additional flexurally rigid plastic rail, for example, which serves as a holder for the bag system at an upper end of the bag. The bordering lines on the side and a bordering line at the lower end of the bag may be formed by welds. In particular for the case when the inner bag and outer bag are formed by flat film tubes, the lateral welds are not absolutely necessary. The lateral bordering lines are then formed by the film fold of the flattened film tube. However, lateral welds are preferred because the welded seam welds to one another the four films of the bag system placed one above the other and thus additionally secures the inner bag in the outer bag.

In such an embodiment of the peripheral weld of the films, the bag system would be composed of a first chamber of the inner bag and two additional chambers of the outer bag which are arranged on the adjacent sides of the inner bag. The outer chambers of the outer bag are in fluidic connection with one another through the through-openings. If the outer bag is filled spent dialyzate for example, in accordance with the outer chambers, flow equalization can be achieved through the openings and the bag can be filled uniformly without resulting in any inadmissible material stresses.

It is possible to provide for the inner or outer chambers to contain additional compartments which are filled with concentrates to prepare the dialysis liquid. Such compartments may be formed, for example, by peelably welded connections of sections of film arranged opposite one another. In particular the opposing films of the inner bag may be peelably welded together so that when the inner bag is filled with diluting liquid, for example, the compartments can be broken open and the concentrates diluted to form the ready-to-use dialysis liquid. The concentrates may be present in a powdered or liquid form or as a dispersion.

The container system described here so far is suitable in particular for a method for producing, preparing, supplying or holding a physiological liquid. A liquid for renal therapy is prepared by filling the internal container of the container system described above. In this step of the method, diluting liquid flows into the interior of the inner bag and due to the filling pressure that builds up it breaks open one or more compartments which are filled with concentrates. The concentrates thereby released are dissolved in the liquid volume, which is continuing to grow due to the influx of the diluent, thus forming the ready-to-use dialysis solution. In another step, liquid is withdrawn from the inner bag through a port for further dilution. The liquid for dialysis processes on a patient may be used in peritoneal dialysis, for example, or in dialysis therapies for extracorporeal blood treatment. Dialysis therapies for extracorporeal blood treatment are also understood to include blood filtration processes, e.g., hemofiltration and hemodiafiltration processes. On the whole, these are understood to include extracorporeal blood therapies, in which components of the blood are removed via filter and the blood is in an exchange relationship with a physiological liquid, either through transmembrane transport or by infusion.

After the liquid has been used, the spent liquid is returned to the outer bag of the bag system. The liquid flows uniformly through the chambers of the outer bag due to the through-passages present in the inner bag. This ensures that the incoming liquid is distributed on both sides of the inner bag. If the outer bag could be filled on only one side because flow equalization to the second half is prevented, this would result in an unwanted double burden on the films and welds. The use of elastic film material in particular has proven suitable for large-volume bags, so the bag reaches its final target volume as in the case of a balloon only by expansion of the films when filled. In such a bag system, uniform filling is especially important to prevent overextension of the film in some sections and the tearing of the film wall associated with it.

DETAILED DESCRIPTION OF THE INVENTION OF THE BASIS OF THE DRAWINGS

Further scope of applicability of the present in will become apparent from the detailed description given hereinafter. However, it should be understood that the detailed description and specific examples, while indicating preferred embodiments of the invention, are given by way of illustration only since various changes and modifications within the spirit and scope of the invention will become apparent to those skilled in the art from this detailed description.

FIG. 1 shows a schematic diagram of a container system without through-openings. The container system consists of an upper outer wall 102a and a lower outer wall 102b (not shown here), which is bordered by a shared peripheral edge 108 and are joined in a fluid-tight manner. In a preferred version, 102a and 102b are the upper and lower film sheets of a bag, and 108 is formed by a permanent weld.

TABLE 1

| Component | Concentrate chamber | Initial weight [g] | Concentration in ready-to-use solution [mmol/L] | Contribution to electric conductivity in solution |
| --- | --- | --- | --- | --- |
| Basic magnesium carbonate 4MgCO$_3$ × Mg(OH)$_2$ × 5H$_2$O | A | 3.01 | 0.5 | essentially none |
| D-Glucose, anhydrous | B | 62 [.62?] | 5.55 | essentially none |
| Calcium chloride anhydrous | A | 8.62 | 1.25 | essentially none |
| Citric acid | A | 11.97 | 1.0 | essentially none |
| Sodium chloride | C | 391.22 | 140 | Yes |
| Sodium bicarbonate | C | 166.78 | 32 | Yes |
| Potassium chloride | A | 28.1 | 2 | essentially none |

The bag has a first concentrate chamber A holding concentrates 105. According to the exemplary embodiments of Table 1, the concentrate chamber A contains the concentrate 105, the substances magnesium carbonate or soluble magnesium salts in general, calcium salts in dissolved or solid form, for example, magnesium chloride and/or calcium chloride, citric acid or citrate salts, acid salts or acids in solid or dissolved form.

A second concentrate chamber C1 holds another concentrate 103a. In one exemplary embodiment, it may be sodium chloride and/or bicarbonate or soluble salts of carbonic acid in general, for example, sodium carbonate or other physiologically tolerable buffers, for example, salts of weak acids.

The concentrate chambers A and C1 are enclosed by a dividing line 109a along a closed circumferential line; in the embodiment shown here, this dividing line consists of a dividing line, which is semipermanent in at least some sections. In one embodiment the first dividing line 109a consists of a peelable seam. The contents of the concentrate chambers A and C1 are separated from one another by the additional dividing line 109b. The additional dividing line 109b may consist of a permanent weld line, a partially semipermanent weld line or a peel seam. The dividing lines 109a and 109b are preferably embodied as peel seams and form a cohesive integral construction of peal seam sections.

The exemplary embodiment according to FIG. 1 is also characterized in that a connecting port 106 connects the filling chamber 110 of the bag to the outside of the bag via a first end in the interior of the bag 106b and another end 106a outside of the bag 101. Port 106 is preferably attached by welded joints in a liquid-tight welded connection in the circumferential dividing line 108. A means 106c for generating liquid turbulence in the inflowing diluent is preferably provided at the end 106b of the port 106. Such means may be embodied as a turbulence-generating nozzle or a turbulence-generating frit. In addition, port 106 consists of a tube passing through the bag in the interior in its longitudinal extent. This ensures that in the filling operation with the bag supported upright, for example, by holding the bag on an upper holding rail 112, the bag is filled from the bottom, and the concentrate chambers A, B, C1, C2 are opened by the internal filling pressure in sequence A simultaneously with B, before C1 at the same time with C2.

Another port 107 with a first end 107a outside of the bag and another end 107b serves to return spent medical liquid, preferably dialysis solution. Port 107 is embodied as a tube in the interior of the bag and is provided so that when the bag is supported in a hanging position, for example, by accommodating the bag on the upper holding rail 112 to pass through the bag along a longitudinal extent. At the location 111, the tube 107 passes through the circumferential line 108 of the bag 101 and opens into another chamber (not shown here), where 111 may be a fluid-tight weld, which secures the bag between the upper and lower bordering planes 102a and 102b and is part of the welded peripheral line 108. The chamber which is not shown here is an enclosing container, preferably a bag which is an integral part of the container system 101. This yields a "bag in bag" design in which the bag holding the ready-to-use liquid is surrounded by a bag holding the spent liquid.

In addition, the embodiment in FIG. 1 shows a second set of concentrate chambers B, C2 which are enclosed by another dividing line along a closed circumferential line 109c. Another dividing line 109d separates the contents of the concentrate chambers B and C2. In a preferred embodiment, the peel seams 109c and 109d form an integral design of peel seam sections developing one into the other.

In the exemplary embodiment, the concentrate 104 in chamber B is a glucose concentrate, for example, in powdered and/or anhydrous and/or liquid form.

Another concentrate chamber C2 with concentrate 103b contains additional substances which are incompatible with the substances of the concentrates 105, 104, i.e., they tend to undergo degradation or enter into unwanted interactions.

This embodiment also shows a peripheral line 108, which preferably consists of a permanent weld. Additional permanent weld lines, sections 108a and 108b, border the container contents or bag contents in such a way as to form an inclined bottom of the interior space. The term "container" here is limited not only to the interior area, which is accessible for a liquid, but parts of the container, which do not belong to the interior space, e.g., from being welded off, and which are not accessible to a liquid, are also covered by this definition of the term container. This design facilitates the development of turbulence in the incoming flow of diluent through means 106c generating liquid turbulence and thus the solution process of the components 105, 104, 103a, 103b. Bartering lines 108c and 108d impart additional stability in the filled state to the filled container, in particular bag. This is important in particular for containers with a large volume in which the internal pressure can act on the circumferential line 108 due to the effect of stress on the quantities contained. Large volume bags in this sense are to be understood as containers having a volume of 5 to 120 liters, 40 to 80 liters, in particular 60 liters±15%.

In one embodiment, the filling chamber is filled through the port 106, dissolving the concentrates from the chambers A, B, C1, C2. To remove the solution thus prepared, the contents for the dialysis therapy are withdrawn via an external pump means, e.g., a tube roll pump or a diaphragm pump. After using the liquid thereby removed, the liquid is returned to the bag system through port 107. The internal bag has a round recess 113 in the opposing films around the port end 107b so that the port end is in fluid connection with the volume of the outer bag. In the worst case the outer bag may fill only one chamber of the outer bag if the passage to the other chamber of the outer bag, for example, remains blocked, e.g., due to folding of the films. In this constellation of FIG. 1, one chamber of the outer bag is always filled further, while the other chamber remains unfilled, so that the filled film chamber is filled beyond the allowed volume, and the film material or the weld lines may be destroyed.

Figure 2:
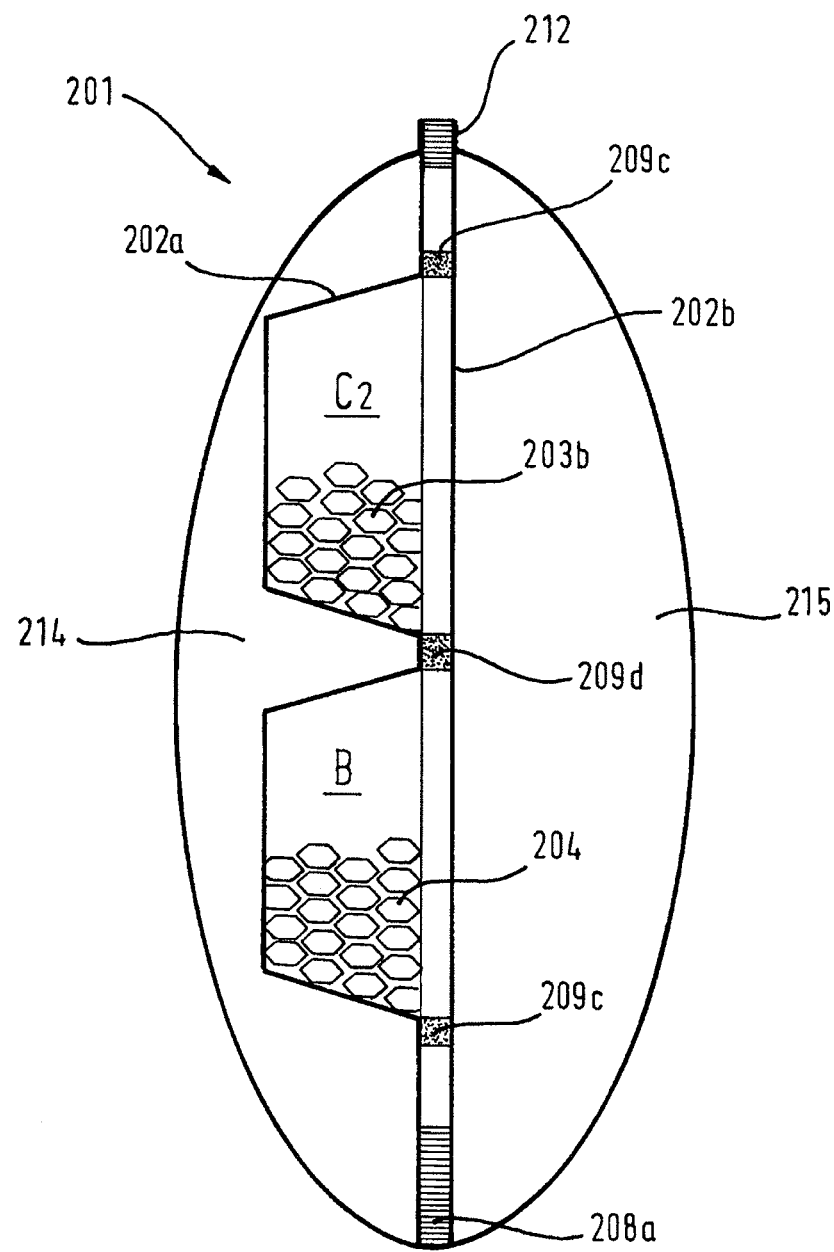

FIG. 2 shows the bag in the unfilled state, i.e., with intact concentrate chambers in a view from the side. The view from the side is shown only schematically and does not show all the details from the frontal view in FIG. 1.

The bag system is thus formed from an inner bag having a film layer 202a (corresponding to 102a) and an opposite film layer 202b (corresponding to 102b FIG. 1). The inner bag is attached to the outer bag by circumferential welding lines (corresponding to 108 FIG. 1). The welding line 208a, like the welding line 108a in FIG. 1, forms the inclined bottom of the inner bag. The inner bag separates the outer bag into two chambers 215 and 214. In addition, FIG. 2 shows schematically the portal access 106, like the concentrate chambers C2 with the concentrate 203b (corresponding to 103b), concentrate chamber B with concentrate 204 (corresponding to 104). In addition, releasable connections 209c and 209d are shown; they are broken open when the inner bag is filled through the port 106 (not shown), allowing the concentrates to mix with the incoming diluting liquid. The mixing solution of the inner bag for use is removed, used and sent to the chambers 215 and 214 for storage via the port 107 (not shown). FIG. 2 shows that when only one chamber of the outer bag, e.g., 215 is filled because, as described above, the access to the second chamber is blocked, this chamber becomes inadmissibly overfilled, which can lead to material fatigue on the bag system.

Figure 3:
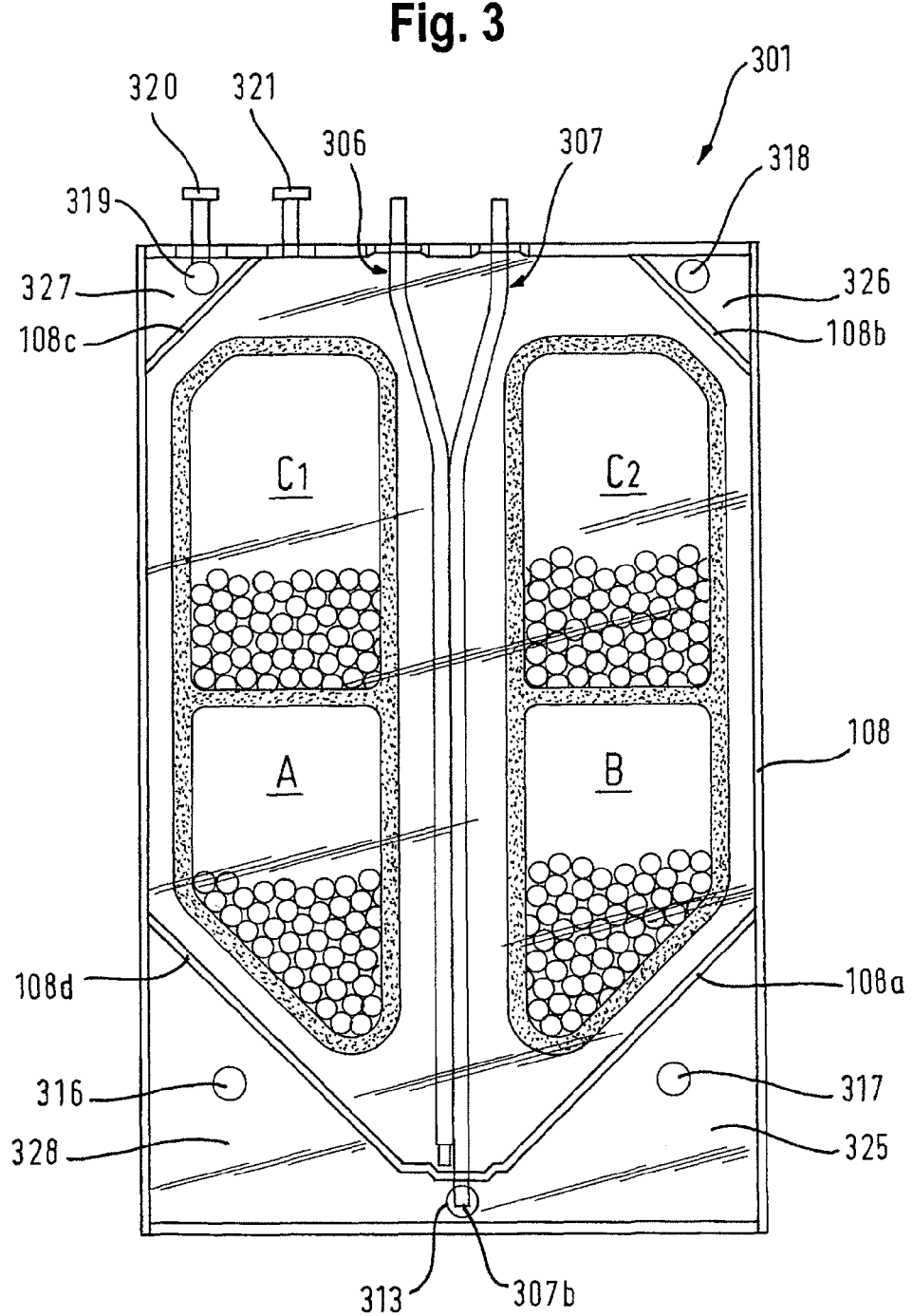

FIG. 3 shows an embodiment according to the invention based on the embodiment in FIG. 1. In addition to the embodiment in FIG. 1, passages 316, 317, 318 and 319 are shown here. The passages are located in the areas 325, 326, 327, 328 of the inner container or the inner bag which are not accessible for liquids. These areas represent areas that are welded off by the permanent welding lines 108, 108a, 108b, 108c, 108d in the exemplary diagram, which do not have any liquid access. Reference is herewith made explicitly to all the other details of the embodiments according to FIG. 1 and FIG. 2.

Initially, as described above, the inner bag is filled with the concentrate chambers A, B, C1, C2, and a ready-to-use solution is prepared. For use, the liquid of the inner bag is removed through the port 306, then used and the spent liquid is filled into the chambers of the outer bag through the port 307, the port end 307b and the recess 313, as shown. The passages 316, 317, 318 and 319 allow a fluidic connection of the chambers in the return of the spent liquid to the chambers of the outer bag. The lower passages 316 and 317 here ensure a fluidic connection of the inflowing liquid. The upper passages 319 and 318 first produce a pneumatic equalization of the air displaced through the incoming liquid. The remaining air is displaced out of the bag system through the two ports 320 and 321. Through the passages 319 and 318 there is thus an equalization of pressure between the two chambers of the outer bag, so that only one port is necessary for the air to be released out of the outer bag. The ports are equipped with hydrophobic filters so that when the filter is wetted the liquid is prevented from leaking out of the bag system. With an increase in the filling of the outer chambers with spend liquid, the passages 319 and 318 may also serve to equalize the flow of the liquid.

If the recess 313 is partially sealed due to folding, for example, and one chamber is filled to a greater extent than the second chamber, then as soon as the liquid level in this chamber has reached a passage 316, 317, 318 or 319, a liquid exchange takes place with the other chamber of the outer bag until reaching a hydrostatic equilibrium. This achieves uniform filling of both chambers surrounding the inner bag.

Figure 4:
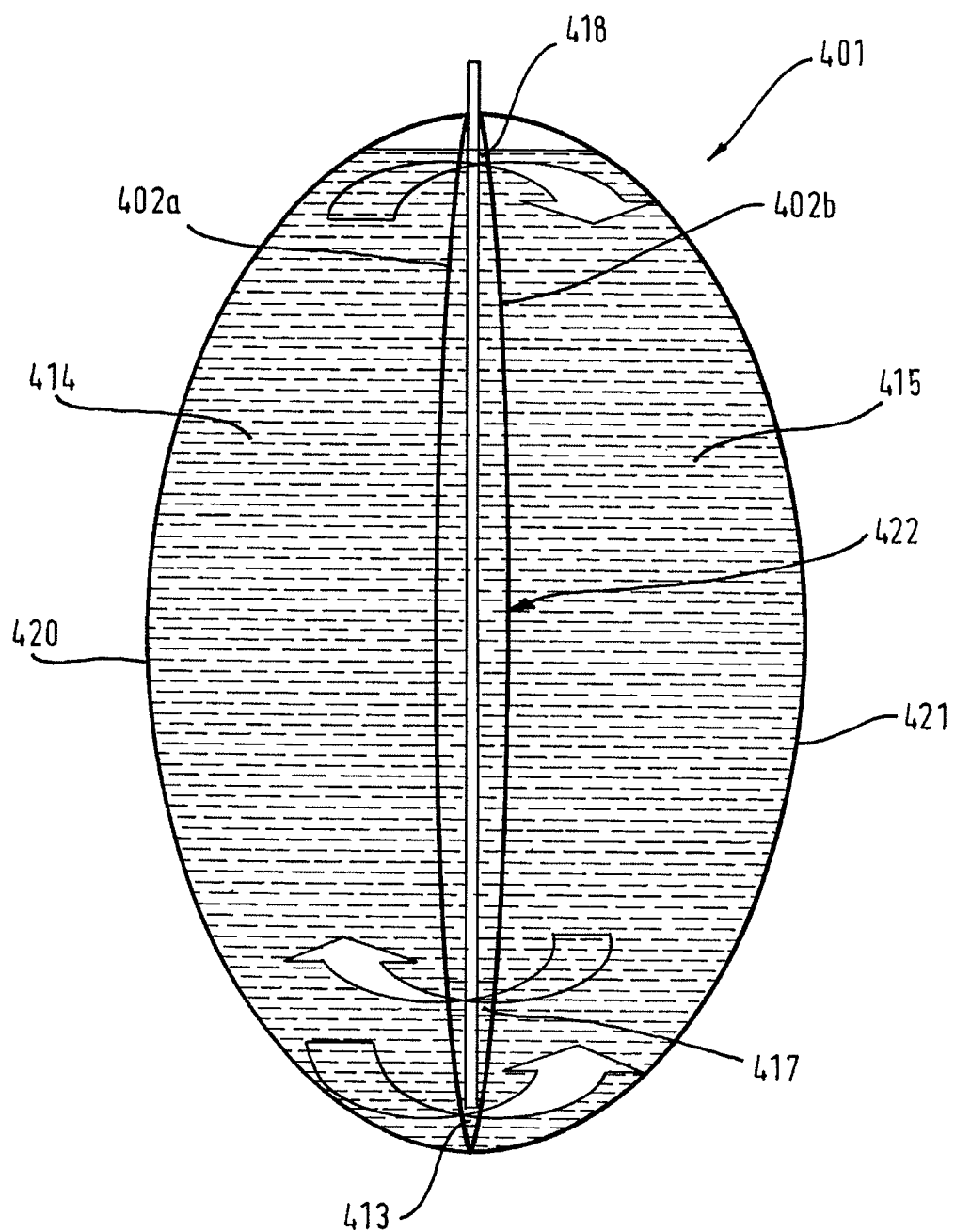

FIG. 4 shows an embodiment of the bag according to the invention in a lateral, cross-sectional view. In this case, the figure shows the inner bag 422 which has already been filled and contains the ready-to-use liquid. Spent liquid is in the chambers of the outer bag 414, 415. The inner bag 422 separates the chambers of the outer bag 420, 421 from one another. In addition, passages 417 and 418 are also shown. The arrows that are shown indicate an overflow of the spent liquid from one chamber into the other chamber of the outer bag. As indicated schematically, the chambers 414, 415 are filled uniformly due to the possibility of overflow or movement of spent liquid between the two chambers. Thus an inadmissible stress on the material with one-sided chamber filling of the outer baa can be prevented.

The invention being thus described, it will he apparent that the same may be varied in many ways Such variations are not to be regarded as a departure from the spirit and scope of the invention, and all such modifications as would be recognized by one skilled in the art are intended to be included within the scope of the following claims.

The invention claimed is:

1. A container system for producing, supplying or holding medical liquids comprising an inner container and an outer container surrounding the inner container with ports that provide access to the inner container and the outer container for filling and/or removing liquids and/or concentrates, said inner container being formed by inner film layers and separating the outer container into two chambers, said inner film layers and outer container sharing a common peripheral seal, said two chambers of said outer containers being in fluid communication with one another via passages or through-openings formed through the inner film layers in areas of the inner container that are not accessible to liquids contained in said inner container.

2. The container system according to claim 1, wherein the inner container is a bag.

3. The container system according to claim 2, wherein the outer container is a bag.

4. The container system according to claim 3, wherein the inner bag and the outer bag are made of an elastically extensible film material.

5. The container system according to claim 1, wherein the through-openings are arranged in at least one of a lower area and an upper area of the container system when the container system is supported upright or in a suspended position.

6. The container system according to claim 1, wherein the inner container and/or the outer container is/are provided with filters which ensure germ-free venting of the containers during filling and/or withdrawal of liquid.

7. The container system according to claim 3, wherein the container system is constructed of at least four films arranged one above the other, having a common bordering line so that an inner chamber corresponding to the volume of the inner bag is formed and the two chambers in the outer bag correspond to the volume of the outer bag.

8. The container system according to claim 7, wherein one of the chambers of the inner bag and/or the outer bag contains one or more compartments filled with concentrates.

9. The container system according to claim 8, wherein one or more compartments of the chambers has/have a bordering structure.

10. The container system according to claim 9, wherein the bordering structure includes peel seams which can be released in the inner bag and/or the outer bag.

11. The container system according to claim 8, wherein the compartments contain powdered water-soluble substances.

12. The container system according to claim 1, wherein the container system has a liquid volume of 5 to 120 liters.

13. The container system according to claim 1, wherein the container system has a liquid volume of 15 to 90 liters.

14. The container system according to claim 1, wherein the container system has a liquid volume of 40 to 80 liters.

15. A container system for producing, supplying or holding medical liquids comprising an inner bag and an outer bag completely surrounding the inner bag, said inner bag separating the outer bag into two chambers, the inner and outer bags having ports that provide access to respective interiors of said bags for filling and/or removing liquids and/or concentrates, said inner bag being formed by inner film layers, said inner film layers and outer bag sharing a common peripheral seal; said two chambers of said outer bag being in fluid communication with one another via passages or through-openings formed through said inner film layers in areas of the inner bag that are not accessible to liquids contained in said inner bag, said passages allowing for equalization of pressure in said two chambers of said outer bag.

16. The container system according to claim 15, wherein said areas of the inner bag that are not accessible to liquids contained in said inner bag are formed by circumferential dividing lines that, form an inclined bottom in the inner bag.

17. The container system according to claim 16, wherein said circumferential dividing lines are formed by permanent welds in said inner film layers.

* * * * *